(12) United States Patent
Stridfeldt et al.

(10) Patent No.: US 10,058,629 B2
(45) Date of Patent: Aug. 28, 2018

(54) ABSORBENT ARTICLE WITH SKIN CARE AGENT COMPOSITION IMMOBILIZED IN A LIPID PHASE

(75) Inventors: Chatrine Stridfeldt, Hovås (SE); Leif Wallström, Göteborg (SE)

(73) Assignee: SCA HYGIENE PRODUCTS AB, Göteborg (SE)

(*) Notice: Subject to any disclaimer, the term of this patent is extended or adjusted under 35 U.S.C. 154(b) by 1210 days.

(21) Appl. No.: 12/093,674

(22) PCT Filed: Dec. 1, 2005

(86) PCT No.: PCT/SE2005/001812
§ 371 (c)(1),
(2), (4) Date: May 14, 2008

(87) PCT Pub. No.: WO2007/064264
PCT Pub. Date: Jun. 7, 2007

(65) Prior Publication Data
US 2008/0300561 A1    Dec. 4, 2008

(51) Int. Cl.
*A61F 13/15*    (2006.01)
*A61F 13/20*    (2006.01)
*A61L 15/44*    (2006.01)
*A61F 13/84*    (2006.01)

(52) U.S. Cl.
CPC .......... *A61L 15/44* (2013.01); *A61F 13/8405* (2013.01); *A61L 2300/452* (2013.01)

(58) Field of Classification Search
CPC .............................. A61F 13/8405; A61L 15/44
USPC .............................. 604/364, 367, 381, 385.01
See application file for complete search history.

(56) References Cited

U.S. PATENT DOCUMENTS

| | | | |
|---|---|---|---|
| 3,489,148 A | 1/1970 | Duncan et al. | |
| 3,585,998 A | 6/1971 | Hayford et al. | |
| 4,011,389 A | 3/1977 | Langdon | |
| 5,059,282 A | 10/1991 | Ampulski et al. | |
| 5,174,027 A | 12/1992 | Gusthalin | |
| 5,609,587 A * | 3/1997 | Roe | 604/360 |
| 5,891,126 A * | 4/1999 | Osborn et al. | 604/385.17 |
| 5,968,025 A | 10/1999 | Roa et al. | |
| 6,153,209 A * | 11/2000 | Vega et al. | 424/404 |
| 6,426,444 B2 | 7/2002 | Roe et al. | |

(Continued)

FOREIGN PATENT DOCUMENTS

DE    33 09 530 C1    10/1984
DE    41 36 540 A1    5/1992

(Continued)

OTHER PUBLICATIONS

Form PCT/ISA/210 (International Search Report) dated Jun. 28, 2006.

(Continued)

*Primary Examiner* — Michele M Kidwell
(74) *Attorney, Agent, or Firm* — Buchanan Ingersoll & Rooney P.C.

(57) ABSTRACT

An absorbent article chosen from the group of diapers, panty liners, sanitary napkins and incontinence guards includes a liquid-pervious first sheet intended to face the wearer, a liquid-impervious second sheet intended to face away from the wearer, and a core part including an absorbent core arranged between the first and second sheets, wherein said core part at least partially is treated with a skincare agent.

23 Claims, 6 Drawing Sheets

(56) References Cited

U.S. PATENT DOCUMENTS

| | | |
|---|---|---|
| 2003/0082970 A1 | 5/2003 | Moberg-Alehammar et al. |
| 2003/0100877 A1 | 5/2003 | Erdman |
| 2004/0024374 A1* | 2/2004 | Hjorth et al. ............ 604/367 |
| 2004/0043049 A1 | 3/2004 | Erdman |
| 2004/0122387 A1 | 6/2004 | Long et al. |
| 2004/0127866 A1 | 7/2004 | Odorzynski |
| 2005/0031847 A1* | 2/2005 | Martens et al. ........ 428/321.5 |
| 2005/0154362 A1* | 7/2005 | Warren et al. ............ 604/367 |
| 2006/0184150 A1* | 8/2006 | Noel ........................ 604/383 |

FOREIGN PATENT DOCUMENTS

| | | | |
|---|---|---|---|
| DE | 201 17 973 U1 | 2/2002 | |
| EP | 0 594 628 B1 * | 12/1999 | ............ A61L 13/15 |
| EP | 1 275 371 A1 | 1/2003 | |
| EP | 1 137 379 A1 | 12/2003 | |
| EP | 1371379 A1 | 12/2003 | |
| WO | WO 96/16681 A1 | 6/1996 | |
| WO | WO 96/016682 A1 | 6/1996 | |
| WO | WO 97/05909 A2 | 2/1997 | |
| WO | WO 98/24931 A1 | 6/1998 | |
| WO | 99/25288 A1 | 5/1999 | |
| WO | WO 99/22684 A1 | 5/1999 | |
| WO | WO 99/45973 A1 | 9/1999 | |
| WO | WO 99/45974 A1 | 9/1999 | |
| WO | WO 99/45976 A1 | 9/1999 | |
| WO | WO 00/64500 A1 | 11/2000 | |
| WO | WO 00/64501 A1 | 11/2000 | |
| WO | WO 00/64502 A1 | 11/2000 | |
| WO | WO 00/64503 A1 | 11/2000 | |
| WO | WO 03/034965 A2 | 5/2003 | |
| WO | 03/053397 * | 7/2003 | ............ A61K 7/50 |

OTHER PUBLICATIONS

Form PCT/ISA/237 (Written Opinion of the International Searching Authority) dated Jun. 28, 2006.

Extended Search Report dated Aug. 24, 2011, in corresponding European Patent Application No. 05812035.3.

European Office Action dated Nov. 2, 2013 in EP Application No. 05 812 035.3.

Office Action dated Apr. 25, 2014 in corresponding patent application No. PI0520712-6 in Brazil (and English-language translation).

* cited by examiner

ABSORBENT ARTICLE WITH SKIN CARE AGENT COMPOSITION IMMOBILIZED IN A LIPID PHASE

FIELD OF INVENTION

The present invention provides an absorbent article comprising a liquid-pervious first sheet, a liquid-impervious second sheet and a core part arranged between the first and second sheets. The core part is comprised of an absorbent core which also contains a skincare agent. In particular, the skincare agent may be administered to a nonwoven strip in the core part somewhere between the first and second sheets. Alternatively, the skincare agent may be included in a lipid phase, preferably as beads arranged between the absorbent core and the first and/or second sheet.

TECHNICAL BACKGROUND

The major function of absorbent articles, such as panty liners, sanitary napkins, incontinence guards as well as diapers is to absorb and contain body exudates. Such articles are thus intended to prevent body exudates from soiling, wetting and otherwise contaminating clothes, bedding or other articles coming in contact with the wearer. Furthermore, the articles are also intended to prevent such body exudates from accumulating on the wearer's skin which, among all, could lead to skin irritations. However, it is difficult to construct absorbent articles that are leaking-proof and fit each and every potential wearer. Another problem with such articles is friction between the article and the skin. Such friction may also cause skin irritation and the problem is particularly significant when the skin is wet.

The problem with leaking absorbent articles and associated contamination and skin irritation problems could be at least partially solved by using lotions and skincare compositions in connection with absorbent products. Such lotions and skincare agents may be added to the skin in order to form a "barrier" so that body exudates do not adhere to the skin. Alternatively, such agents may directly prevent/treat skin irritation by adding skin-friendly lipid formulations and/or anti-bacterial formulations. WO 03/034965 discloses an insert that is intended to be used together with an absorbent article. The insert has a first surface treated with a skincare agent and a second surface impermeable to said skincare agent. Such an insert can be arranged in a flexible way in relation to the absorbent product but it is also more complicated to use several products simultaneously compared to just one product. Moreover, a solution according to WO 03/034965 may also produce more waste.

Similarly, DE-U-201 17 973 relates to tissue which could be used as an insert in connection with diapers. The tissue consists of a fleece material coated with a solid skincare compound. Hence, the subject matter of DE-U-201 17 973 is also more complicated to use for the consumer and leads to more waste as more components are used simultaneously.

U.S. Pat. No. 6,426,444B2, describes an absorbent disposable article, such as a diaper, where at least a portion of the liquid-pervious hydrophilic top sheet comprises a lotion coating to reduce adherence of bowel movements to a wearer's skin. The lotion is applied to the top sheet as stripes that are separated by stripes having no lotion. Because the lotion is located on the outside of the article, there is a risk that the lotion layer would come off before the article is worn.

WO-00/124748 presents an absorbent article wherein at least a portion of the article has a skincare composition. The article also comprises a barrier sheet that is treated to reduce migration of said skincare composition.

WO98/24931 discloses an absorbent article having barrier leg cuffs along the edges of said article. At least a part of the leg cuffs are coated with a lotion intended to be transferred to a wearer upon use. Because the lotion is located on the outside of the article, there is a risk that the lotion layer would come off before the article is worn.

US, A, 20030100877 and US, A, 20040043049 both relate to absorbent products wherein a skincare ingredient is included in the adhesive used for manufacturing the products. The adhesive is at least partially dissolved upon release of said skincare ingredient which in turn could lead to reduced strength of the absorbent product.

It is also known to include auxiliary components such as odour control systems in absorbent products. Such absorbent products are described in US, A, 2004/0122387 and US, A, 2004/0127866. These documents disclose several alternatives for odour control. Odours may be absorbed by e.g. zeolites or oxidized by oxidation agents embedded in adjacent to the absorbent core of the absorbent article. In this case, nothing is released from the odour control system. Alternatively, gaseous fragrant substances may be released. Nothing is disclosed about releasing skincare compositions.

OBJECT AND SUMMARY

Accordingly, there is a need for improved ways of administering skincare compositions in connection with absorbent products.

The above mentioned problems are solved according to the present invention by providing an absorbent article including a liquid-pervious first sheet, a liquid-impervious second sheet and a core part arranged between the first and second sheet, where the core part is at least partially treated with a skincare agent.

BRIEF DESCRIPTION OF THE DRAWINGS

The embodiments of the invention will now be described with reference to the enclosed figures, in which FIG. 1 discloses an absorbent product according to an embodiment of the present invention, in particular a sanitary napkin, wherein strips treated with a skin care agent is arranged between the absorbent core and a liquid previous sheet.

DETAILED DESCRIPTION OF THE PREFERRED EMBODIMENTS

As disclosed herein, the term "absorbent article" relates to an absorbent article chosen from the group of panty liners, sanitary napkins, incontinence guards and diapers. The absorbent article is comprised of a liquid-pervious first sheet intended to face the wearer and a liquid-impervious second sheet intended to face away from the wearer.

As disclosed herein, the term "core part" relates to the part of the absorbent article that is enclosed between the first and second sheets. As disclosed herein, the term "absorbent core" relates to part of the core part that is able to absorb or retain virtually all liquid absorbed by the absorbent product.

As disclosed herein, the term "skin care agent" relates to an agent that has a beneficial impact on skin. It may for example soften the skin, be useful for treating skin problems, etc.

As disclosed herein, the term "lipid phase" relates to a water-insoluble organic phase with a fatty character. Lipids suitable to be used in the lipid phase of the invention include petroleum-derived lipids, synthetic lipids, and animal- and plant-derived lipids.

As mentioned above, the disclosure relates to an absorbent article chosen from the group of panty liners, sanitary napkins, incontinence guards and diapers. The absorbent article is comprised of a liquid-pervious first sheet intended to face the wearer and a liquid-impervious second sheet intended to face away from the wearer.

The first sheet is preferably compliant, soft feeling and non-irritating to the wearer's skin. Further, the first sheet is, as already mentioned, liquid-pervious, permitting liquids (e.g. body exudates, such as menses and/urine) to readily penetrate through its thickness. A suitable first sheet may be manufactured from a wide range of materials such as woven and nonwoven materials (e.g., a nonwoven web of fibres); polymeric materials such as apertured formed thermoplastic films, apertured plastic films, and hydroformed thermoplastic films; porous foams, reticulated foams; reticulated thermoplastic films; and thermoplastic scrims. Suitable woven and nonwoven materials can be comprised of natural fibres (e.g., wood or cotton fibres), synthetic fibres (e.g., polymeric fibres such as polyester, polypropylene, or polyethylene fibres) or from a combination of natural and synthetic fibres. When the first sheet comprises a nonwoven web, the web may be spunbonded, carded,wet-laid, melt-blown, hydroentangled, combinations of above, or the like.

As already mentioned, the second sheet is impervious to liquids (e.g., body exudates, such as menses and/or urine), and is manufactured from a thin plastic film or other flexible liquid-impervious materials known to the skilled person. The second sheet prevents the exudates absorbed and contained in the core part from wetting articles which contacts the absorbent article. The second sheet may thus comprise a woven or nonwoven material, polymeric films such as thermoplastic films of polyethylene or polypropylene or composite materials such as film-coated non-woven material. Further, the second sheet may permit vapours to escape from the core part (i.e., the second sheet is breathable) while still preventing exudates from passing through the second sheet. Such sheets are well-known in the art.

The absorbent article also comprises a core part, which in turn consists of an absorbent core and optionally an auxiliary component. The core part is arranged between the first and second sheets.

The absorbent core is capable of absorbing or retaining liquids (e.g., body exudates, such as menses and/or urine). The absorbent core is preferably compressible, conformable, and non-irritating to the wearer's skin. The absorbent core may be manufactured in a wide variety of sizes and shapes. The absorbent core may include any of a wide variety of liquid-absorbing materials commonly used in absorbent articles, such as air felt, creped cellulose wadding, melt-blown polymers, chemically stiffened, modified or cross-linked cellulosic fibres, synthetic fibres, tissue, absorbent foams, superabsorbent polymers or any equivalent material or combination of materials, or mixture of these. The configuration and construction of the absorbent core may also be varied in accordance with the state of the art.

The auxiliary component is a component that is able to store and release useful agents through said liquid-pervious first sheet. Examples of such auxiliary components are strips or lipid preparations.

The core part is at least partially treated with a skincare agent.

Skin Care Agents

The skin care agents are solid, or more often semisolid, at 20° C., i.e. at ambient temperatures. By "semisolid" is meant that the composition of the skin care agent has a rheology typical of pseudoplastic or plastic fluids.

When no shear is applied, the skin care compositions can have the appearance of a semi-solid but can be made to flow as the shear rate is increased. This is due to the fact that, while the skin care composition contains primarily solid components, it also includes some minor liquid components.

The skin care compositions are at least semi-solid at room temperature to minimize migration of the skin care agent. In addition, the skin care compositions preferably have a final melting point (100% liquid) above potential "stressful" storage conditions that can be greater than 45° C.

Preferably, 2-50% of the present skin care composition should be liquid at 20° C., and 25-95% of the composition should be liquid at 37° C. The final melting point should be above 38° C. In a still more preferred embodiment of the invention 3-25% of the composition should be liquid at 20° C., and 30-90% of the composition should be liquid at 37° C. In this embodiment, the final melting point should be above 45° C. By being solid or semisolid at ambient temperatures, these skin care compositions do not have a tendency to flow and migrate out to the external surfaces of into the interior of the diaper to which they are applied.

The skin care agent compositions may comprise. (1) an emollient(s); (2) an immobilizing agent(s) for the emollient; (3) optionally a hydrophilic surfactant(s); and (4) other optional components.

The viscosity at 20° C. of the formulated skin care agent compositions, including emollient, immobilizing agent, and optional components should be as high as possible to keep the lotion from flowing out from the interior of the absorbent product. Unfortunately, high viscosities can also lead to skin care agent compositions that are difficult to apply without processing problems. Therefore, a balance must be achieved so the viscosities are high enough to keep the skin care agent compositions in desired locations in the absorbent product. Suitable viscosities for the skin care agent compositions will typically range from about 1 to about 5000 centipoises, preferably from about 5 to about 200 centipoises, more preferably from about 10 to about 100 centipoises measured at 60° C.

The key active ingredient in these skin care agent compositions is one or more emollients. As used herein, an emollient is a material that softens, soothes, supples, coats, lubricates, moisturizes, or cleanses the skin. An emollient typically accomplishes several of these objectives such as soothing, moisturizing, and lubricating the skin. These emollients have either a plastic or fluid consistency at 20° C., i.e., at ambient temperatures. This particular emollient consistency allows the skin care agent composition to impart a soft, lubricious, lotion-like feel.

The useful emollients are also substantially free of water. By "substantially free of water" is meant that water is not intentionally added to the emollient. Addition of water to the emollient is not necessary in preparing or using the skin care agent compositions and could require an additional drying step. However, minor or trace quantities of water in the emollient that are picked up as a result of, for example, ambient humidity can be tolerated without adverse effect. Typically, the emollients contain about 5% or less water, preferably about 1% or less water, most preferably about 0.5% or less water.

Emollients can be petroleum-based, fatty acid ester type, alkyl ethoxylate type, fatty acid ester ethoxylates, fatty alcohol type, polysiloxane type, or mixtures of these emollients. Suitable petroleum based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for skin care agent compositions.

Suitable fatty acid ester type emollients include those derived from $C_{12}$-$C_{28}$ fatty Acids, preferably $C_{16}$-$C_{22}$ saturated fatty acids, and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate and mixtures thereof.

Suitable fatty acid ester emollients can also be derived from esters of longer chain fatty alcohols ($C_{12}$-$C_{28}$, preferably $C_{12}$-$C_{16}$) and shorter chain fatty acids e.g., lactic acid, such as lauryl lactate and cetyl lactate.

Suitable alkyl ethoxylate type emollients include $C_{12}$-$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23.

Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth10 (a stearyl alcohol ethoxylate having an average degree of ethoxylation of 10).

These alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1 A.

Suitable fatty alcohol type emollients include $C_{12}$-$C_{22}$ fatty alcohols, preferably C16-C18 fatty alcohols. Representative examples include cetyl alcohol and stearyl alcohol, and mixtures thereof. These fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 12.

Other suitable types of emollients include polysiloxane compounds. In general suitable polysiloxane materials include those having monomeric siloxane units of the following structure:

wherein, R1 and R2, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. R1 and R2 radicals of any particular monomeric unit may differ from the corresponding functionalities of the next adjoining monomeric unit. Additionally, the polysiloxane can be either a straight chain, a branched chain or have a cyclic structure. The radicals R1 and R2 can additionally independently be other silaceous functionalities such as, but not limited to siloxanes, polysiloxanes, silanes, and polysilanes. The radicals R1 and R2 may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like.

Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the absorbent product. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about to about 1000 centistokes. High viscosity polysiloxanes which themselves are resistant to flowing can be effectively deposited in the absorbent product by such methods as, for example, emulsifying the polysiloxane in surfactant or providing the polysiloxane in solution with the aid of a solvent, such as hexane, listed for exemplary purposes only. Particular methods for applying polysiloxane emollients to absorbent products are discussed in more detail hereinafter.

Preferred polysiloxanes compounds are disclosed in U.S. Pat. No. 5,059,282. Particularly preferred polysiloxane compounds for use as emollients in the lotion compositions include phenyl-functional polymethylsiloxane compounds (e.g., Dow Corning 556 Cosmetic-Grade Fluid: polyphenylmethylsiloxane), dimethicone compounds, and cetyl or stearyl functionalized dimethicones such as Dow 2502 and Dow 2503 polysiloxane fluids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Besides petroleum-based emollients, fatty acid ester emollients, fatty acid ester ethoxylates, alkyl ethoxylate emollients fatty alcohol emollients, and polysiloxanes, the useful emollients can include minor amounts (e.g., up to about 10% of the total emollient) of other, conventional emollients. These other conventional emollients include, but are not limited to propylene glycol, glycerine, triethylene glycol, spermaceti or other waxes, fatty acids, and fatty alcohol ethers having from 12 to 28 carbon atoms in their fatty chain, such as stearic acid, propoxylated fatty alcohols; glycerides, acetoglycerides, and ethoxylated glycerides of $C_{12}$-$C_{28}$ fatty acids; other fatty esters of polyhydroxy alcohols; lanolin and its derivatives, and cod liver oil.

These other emollients should be included in a manner such that the solid or semisolid characteristics of the skin care agent composition are maintained. The amount of emollient that can be included in the skin care agent composition will depend on a variety of factors, including the particular emollient involved, the lotion-like benefits desired, the other components in the composition and like factors. The skin care agent composition can comprise from about 10 to about 95% of the emollient. Preferably, the composition comprises from about 20 to about 80%, most preferably from about 40 to about 75%, of the emollient.

An especially key component of the skin care agent compositions is an agent capable of immobilizing the emollient in the absorbent product to which the skin care composition is applied. Because the emollient in the composition has a plastic or fluid consistency at 20° C., it tends to flow or migrate, even when subjected to modest shear. Accordingly, in some situations, an immobilizing agent has to be added in order to achieve the melting characteristics of a skin care agent.

In addition to being miscible with (or solubilized in) the emollient, the immobilizing agent needs to have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° C. to about 150° C.

Suitable immobilizing agents for the present invention can comprise a member selected from the group consisting of $C_{14}$-$C_{22}$ fatty alcohols, $C_{12}$-$C_{22}$ fatty acids, and $C_{12}$-$C_{22}$ fatty alcohol ethoxylates having an average degree of ethoxylation ranging from 2 to about 30, and mixtures thereof. Preferred immobilizing agents include $C_{16}$-$C_{18}$ fatty alcohols, most preferably selected from the group consisting of cetyl alcohol, stearyl alcohol, and mixtures thereof.

Mixtures of cetyl alcohol and stearyl alcohol are particularly preferred. Other preferred immobilizing agents include $C_{16}$-$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$-$C_{18}$ fatty alcohol ethoxylates having an average degree of ethoxylation ranging from about 5 to about 20. Preferably, the fatty alcohols, fatty acids and fatty alcohols are linear.

Importantly, these preferred immobilizing agents such as the $C_{16}$-$C_{18}$ fatty alcohols increase the rate of crystallization of the lotion causing the lotion to crystallize rapidly onto the surface of the substrate. Lower lotion levels can therefore be utilized or a superior lotion feel can be delivered. Traditionally, greater amounts of lotion were needed to generate softness because of the flow of these liquids into the diaper core.

Other types of immobilizing agents can be used either alone or in combination with the fatty alcohols, fatty acids, and fatty alcohol ethoxylates described above. Examples of these other types of immobilizing agents include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using diaper leg cuffs to which the lotion composition is applied, these esters and amides should also be relatively mild and non-irritating to the skin.

Suitable polyhydroxy fatty acid esters will have the formula: $[R'COO]_n$—Y, wherein R is a $C_5$-$C_{31}$ hydrocarbyl group, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters comprises certain sorbitan esters, preferably the sorbitan esters of $C_{16}$-$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and triester versions of these sorbitan esters, e.g., sorbitan mono-, di- and tripalmitate, sorbitan mono-, di- and tri-stearate, sorbitan mono-, di and tribehenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and diesters are usually the predominant species in these mixtures.

Another class of suitable polyhydroxy fatty acid esters comprises certain glyceryl monoesters, preferably glyceryl monoesters of $C_{16}$-$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species.

Another class of suitable polyhydroxy fatty acid esters comprise certain sucrose fatty acid esters, preferably the $C_{12}$-$C_{22}$ saturated fatty acid esters of sucrose. Sucrose monoesters and diesters are particularly preferred and include sucrose mono- and di-stearate and sucrose mono- and di-laurate.

Suitable polyhydroxy fatty acid amides will have the formula: $R^2$—CO—$NR^1$—Z, wherein $R^1$ is H, $C_1$-$C_4$ hydrocarbyl, 2-hydroxyethyl, 2-hydroxypropyl, methoxyethyl, methoxypropyl or a mixture thereof, preferably $C_1$-$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and R2 is a $C_5$-$C_{31}$ hydrocarbyl group, preferably straight chain $C_7$-$C_{19}$ alkyl or alkenyl, more preferably straight chain $C_9$-$C_{17}$ alkyl or alkenyl, most preferably straight chain $C_{11}$-$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,027, which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose.

High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —CH($CH_2OH$)—$[(CHOH)_n-1]$—$CH_2OH$, —$CH_2OH$—$CH_2(CHOH)_2(CHOR^3)(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-2-ethoxypropyl or N-2-hydroxypropyl.

$R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1 deoxymaltityl, 1-deoxylactityl, 1-deoxygalactityl, 1-deoxymannityl, 1-deoxymaltotriotityl, etc. The most preferred polyhydroxy fatty acid amides have the general formula:

$R^2$—CO—$NR^1$—$CH_2$—$[CHOH]_4$—$CH_2$—OH wherein $R^1$ is methyl or methoxypropyl; $R^2$ is a $C_{11}$-$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}$($OCH_2CH_2)_n$OH, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, beeswax, candelilla, paraffin, ceresin, esparto, ouricuri, rezowax, and other known waxes. Preferably the wax is a paraffin wax.

An example of a particularly preferred paraffin wax is Parrafin S.P. 434 from Strahl and Pitsch Inc. P.O. Box 1098 West Babylon, N.Y. 11704 (USA).

The amount of immobilizing agent that should be included in the skin care agent compositions will depend on a variety of factors, including the particular emollient involved, the particular immobilizing agent involved, whether an emulsifier is required to solubilize the immobilizing agent in the emollient, the other components in the lotion composition and like factors. The composition can comprise from about 5 to about 90% of the immobilizing agent.

Preferably, the skin care agent composition comprises from about 5 to about 50%, most preferably from about 10 to about 40%, of the immobilizing agent.

Depending upon the particular immobilizing agent used in the skin care agent composition, an additional hydrophilic surfactant (or a mixture of hydrophilic surfactants) may optionally be used to improve processability and/or stability of the compositions.

Suitable hydrophilic surfactants will be miscible with the emollient and the immobilizing agent so as to form homogeneous mixtures. Because of possible skin sensitivity of those using disposable absorbent products to which the skin care agent composition is applied, these surfactants should also be relatively mild and non-irritating to the skin. Typically, these hydrophilic surfactants are non-ionic to be not only non-irritating to the skin, but also to avoid other undesirable effects on any underlying tissue laminate structure, e.g., reductions in tensile strength.

Suitable non-ionic surfactants may be substantially non-migratory after the lotion composition is applied to the diaper leg cuffs and will typically have HLB values in the range of from about 4 to about 20, preferably from about 7 to about 20. To be non-migratory, these non-ionic surfactants will typically have melt temperatures greater than the temperatures commonly encountered during storage, shipping, merchandising, and use of disposable absorbent products, e.g., at least about 300° C. In this regard, these non-ionic surfactants will preferably have melting points similar to those of the immobilizing agents previously described. Suitable non-ionic surfactants for use in lotion compositions of the present invention include alkyl-glycosides; alkyl-glycoside ethers as described in U.S. Pat. No. 4,011,389; alkylpolyethoxylated esters such as Pegosperse 1 OOOMS (available from Lonza, Inc., Fair Lawn, N.J., USA), ethoxylated sorbitan mono-, di- and/or tri-esters of $C_{12}$-$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product Of $C_{11}$-$C_{15}$ linear alcohols with 9 moles of ethylene oxide), marketed by Union Carbide Corporation; KYRO EOB (condensation product of $C_{13}$-$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$-$C_{15}$ linear alcohols with 12 moles of ethylene oxide) and NEODOL 23-6.5T (condensation product of $C_{12}$-$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL, 25-12, can also function as alkyl ethoxylate emollients).

Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about to about 20 may also be used as the hydrophilic surfactant.

Another type of suitable surfactant includes Aerosol OT, a dioctyl ester of sodium sulfosuccinic acid marketed by American Cyanamid Company.

Still another type of suitable surfactant includes silicone copolymers such as General Electric SIF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the lotion composition.

The amount of hydrophilic surfactant required to improve the processability and/or stability of the lotion composition will depend upon the type of emollient and immobilizing agent used, the HLB value of the surfactant used and like factors. The lotion compositions can optionally comprise from about 1 to about 50% of the hydrophilic surfactant, more preferably from about 1 to about 25%, by weight of the hydrophilic surfactant.

Skin care agent compositions can comprise other optional components typically present in emollient, creams, and lotions of this type. Examples of such components include substances which adsorb irritating components in urine or excrement, such as clay mineral (bentonite, keolin, montmorillonite, etc), silicon oxide compounds (quartz, zeolites, water glass, etc) or activated charcoal. The substances can advantageously have been activated to be more adsorbent by means of various treatments, for example with quaternary ammonium compounds.

Other such optional components are enzyme inhibitors. Examples of such inhibitors are metal salts of iron or zinc, trace amounts of heavy metal ions such as copper or silver, ethylene diamine tetreacetic acid (EDTA), soybean trypsin inhibitor, lima bean protease inhibitor, maize protease inhibitor, stearylglycyrrhetinate, 30 glycerol triacetate, betaine compounds, sulphobetaine compounds, cholestyramine, p-guanidinobenzoates.

Furthermore, skincare agent compositions can optionally include pH-regulating additives, for example organic or inorganic acids such as adipic acid, ascorbic acid, benzoic acid, citric acid, malic acid, tartaric acid, lactic acid, phosphoric acid or hydrochloric acid. Furthermore, useful buffers are made from said acids with corresponding salts. The buffers may also include polymeric acids, for example polyphosphoric acid or polyacrylic acid.

Skin care agent compositions can also optionally include additions of probiotic micro-organisms, characterized by being antagonistic towards undesired micro-organisms, e.g. urinary tract pathogens or skin infection pathogens. Examples of probiotic micro-organisms which can be used are individual strains or mixtures of several strains of lactic acid bacteria taken from the species *Lactobacillus* acidophilus, Lactobacillus curvatus, Lactobacillus plantarum or *Lactococis lactis*. Skin care agent compositions can also include more or less active substances such as: Anti-inflammatory agents, e.g. acetylsalicylic acid, allantoin, azulen, alpha bisabolol (chamomile), flavonoids, glycyrrhizinic acid, ichthammol (Inotyol@)), tannins. Astringents (vasoconstrictors), for example TiO, ZnO (and other Zn 20 compounds), aluminium acetate solution, aluminium tartrate solution (and other Al compounds), ethanol or ethanol-based solutions.

Further optional components may be selected from alphahydroxy acids (citric acid, tartaric acid, lactic acid, malic acid, etc.), ascorbic acid (vitamin C), vitamin A compounds (retinol, retinal, tretinoin and isotretinoin), avocado sterols, 25 betaine (trimethylgiycine), ceramides, grapeseed extract, essential fatty acids, flavonoids, phytosphingosine, phytosterols, hyaluronic acid, yeast extract, chitosan, milk protein (Lactis proteinum), pantenol (provitamin B5), polysaccharides, tocopherol (vitamin E), ubiquinone (coenzyme Q10), pectin and urea.

Further optional components may be selected from perfume oils and also active components isolated from plants, for example mixtures of natural and synthetic fragrances. Natural fragrances are extracts from flowers such as aloe vera (Aloe barbadensis), algae extract, rosemary extract, (lily, lavender, rose, jasmine, neroli, ylangylang), I stems and leaves (geranium, patchouli, petitgrain), fruits (aniseed, coriander, cumin,: 20 juniper), fruit peels (bergamot, lemon, orange), roots (mace, angelica, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and 25 castorerum. Typical synthetic fragrance compounds are products of the ester, ether, aldehyde, ketone, alcohol and hydrocarbon type. Fragrance compounds of the ester type are e.g. benzyl acetate, phenoxyethyl isobutyrate, p-tert-butyleyclohexyl acetate, linalyl I acetate, dimethylbenzylcarbinyl acetate, phenylethyl acetate, linalyl benzoate, benzyl formate, ethyl methylphenviglycinate, allyl cyclohexylpropionate, styrallyl propionate and 30 benzyl salicylate. It is preferred to include aloe vera in the compositions.

The ethers include, for example, benzyl ethyl ether, the aldehydes include, for example the linear alkanals having 8 to 18 carbon atoms, citral, citronella, citronellyloxyacetaldehyde, cyclamenaldehyde, hydroxycitronellal, filial and bourgeonal, the 35 ketones include, for example, the ionones, a-isomethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams.

Preference is, however, given to using mixtures of different fragrances, which together produce a pleasing scent note. Essential oils of lower volatility, which are mostly used as flavor components, are also suitable as perfume oils, e.g. sage oil, camomile oil, oil of cloves, balm oil, mint oil, cinnamon leaf oil, lime blossom oil, juniperberry oil, vetiver oil; olibanum oil, galbanum oil, labolanum oil and lavandin oil. Preference is given to using bergamot oil, dihydromyrcenol. filial, Iyral, citronellol, phenylethyl alcohol, a hexylcinnamaldehyde, geraniol, benzylacetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, p-damascone, geranium oil bourbon, eyclohexyl salicylate, Vertofix Coeur, Iso-E-Super, Fixolide NP, Evernyl, iraldein gamma, phenylacetic acid, geranyl acetate, benzyl acetate, rose oxide, Romillat, Irotyl and 10 Floramat, alone or in mixtures.

A list of suitable ingredients for skin conditioning agents can be obtained from the CTFA (The Cosmetie, Toiletry and Fragrance Association).

Furthermore, antimicrobial agents, for example amorolfin, antibiotics, bacitracin, benzalkonium chloride, benzetonium chloride, cetrimide, fusidic acid, gentian violet (methyirosaniline chloride), hexachlorophene, hexylresorcinol, imidazole derivataties (for example biphonazole, econazole, ketoconazole, chlotrimazole, miconazole), chlorhexidine, nystatin, povidone-iodine, i terbinafin, triclosan, and hydrogen peroxide may be included.

Furthermore, antiviral agents, for example acyclovir, imiquimod, podophyllotoxin, podophilox, cidofovir, penciclovir, vidarabin, idoxuridine, trifluridine, tromantadine, and lamivudine, may be included.

The skin care agent compositions may also optionally include glucocorticoids, preferably of low potency, for example hydrocortisone, or antipruritic, for example antihistamines or local anaesthetics (e.g. lidocaine).

The skin care agent compositions may also optionally comprise ready-made mixtures of skin ointments, creams and lotions. For example, Necesse Lotion (ingredients: aqua, propylene glycol, liquid paraffin, octyl octanoate, urea, PEG-8 distearate, steareth-2, steareth-21, betaine, lactic acid, tocopheryl acetate, dimethicone, tromethamine, methyl paraben, propylparaben, perfume), Necesse® Skin Cream (ingredients: aqua, liquid paraffin, octyl stearate, sodium chloride, urea, glyceryl stearate, stearic acid, ceteary1 alcohol, PEG-30 stearate, tocopheryl acetate, tromethamine, dimethicone, methylparaben, sorbic acid, propylparaben, perfume), Necesse® Barrier Cream (ingredients: petrolatum, glycerol, Arachis hypogaea, triethyl citrate, tocopheryl acetate) or Necesse® Zinc Ointment (ingredients: petrolatum, Arachis hypogaea, zinc oxide, retinyl 25 palmitate, tocopherol). Necesse® products are sold commercially by SCA Hygiene Products, Gothenburg, Sweden.

Other examples of some different substances that optionally may be used are described partially inter alla in the 14 following documents: WO 96/16682, WO 96/16681, WO 97/05909, WO 99/45973, WO 99/45974, WO 99/45976, DE 33 09 530 C1, DE 41 36 540 A1, U.S. Pat. No. 3,489,148 "Topsheet for disposable diapers" (Duncan et al.), WO 00/64502, WO 00/64501, WO 00/64500, WO 00/64503, and WO 99/22684.

Auxiliary Component

Preferably, the skincare agent is only present in an auxiliary component of the core part and not present in the absorbent core.

In a preferred embodiment, the auxiliary component of the core part is a nonwoven strip. The skincare agent can be continuously applied to the strip, or alternatively it can be applied to the strip in discrete positions. It is also preferred that nonwoven strip at least partially surrounds the absorbent core. The nonwoven strip may be manufactured of the same kind of materials that are disclosed in connection with the description of the first sheet above.

As mentioned above, the auxiliary component may also be a lipid preparation, or a lipid phase. In this case, the skincare agent is included in the lipid phase. Furthermore, the skincare agent is immobilised inside the lipid phase as long as said phase is in solid state, which means that undesired spreading of the skincare agent can be avoided below the melting temperature of the lipid phase. Accordingly, it is advantageous to use such a phase that is substantially solid at a temperature of 25° C., and preferably is in a substantially liquid state at a temperature of 37° C. The lipid phase will then be solid when the absorbent article is stored but it will melt upon use and the skincare agent will be released. As the skin temperature of the wearer will be higher when the wearer is physically active, a larger amount of skincare agent will be released when a larger amount is needed.

When a lipid phase is included as auxiliary component, it is advantageously present as beads in the absorbent article. Smaller beads melt quicker than larger beads and whole layers as a response to increased temperatures, and the skincare agent is therefore released exactly when it is needed. Furthermore, it is relatively easy to arrange beads in suitable positions in an absorbent article.

Typically the bead size is within the range from 0.5 mm-5 mm.

In a preferred embodiment said core part is treated with a skincare agent in a part intended to face the inner part of the thigh of the wearer.

In a preferred embodiment said core part is treated with a skin care agent in locations close to edges or wings of the article.

EXAMPLES

The following examples are provided for illustration purposes only and are not intended to limit the scope of the invention in any way.

Example 1

Figure 1:
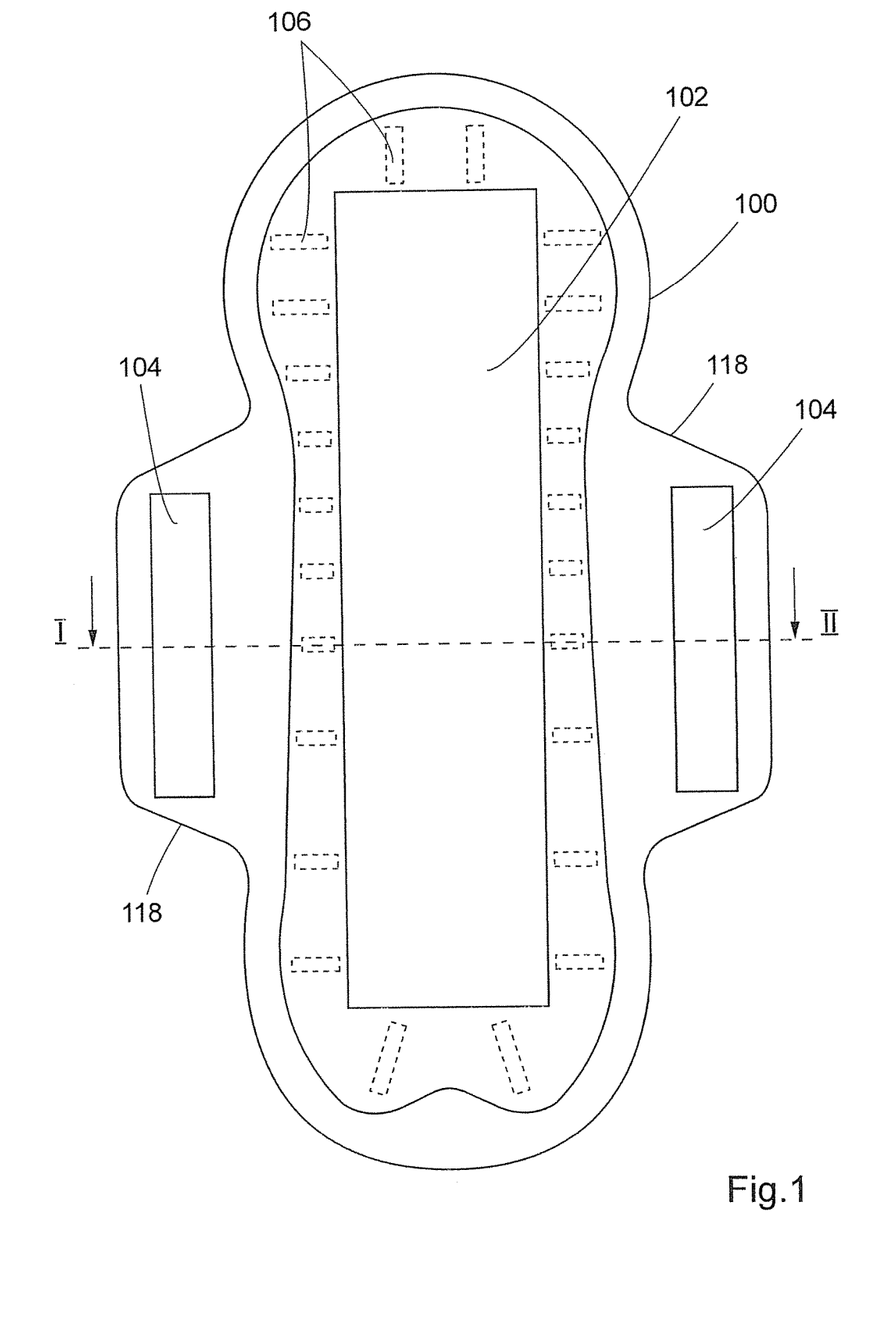
Figure 2:
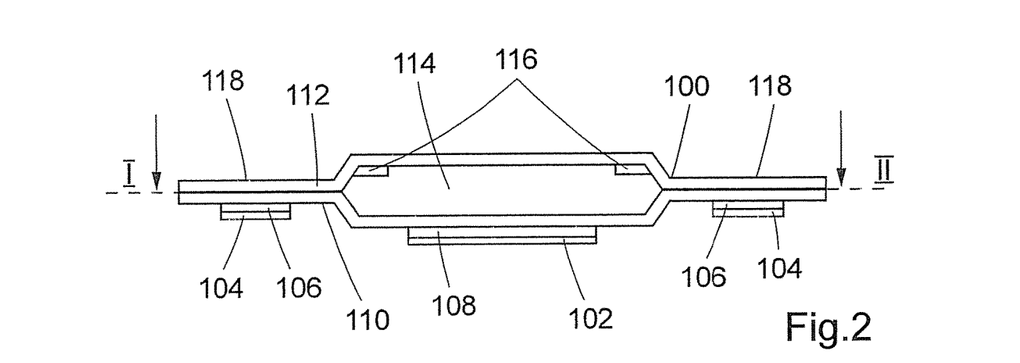
FIG. 2 shows a cross-section along I-II of the sanitary napkin of FIG. 1.

FIGS. 1 and 2 relate to a sanitary napkin 100 comprising a liquid-pervious first sheet 112 intended to face the wearer, and a liquid-impervious second sheet 110 intended to face away from the wearer. Strips 116 treated with a skin care agent are arranged between the absorbent core 114 and the first sheet 112. Adhesive parts 106, 108 covered by release paper 102, 104 are arranged on the second sheet 110 in the central part and on the wings 118.

Example 2

Figures 3, 5:
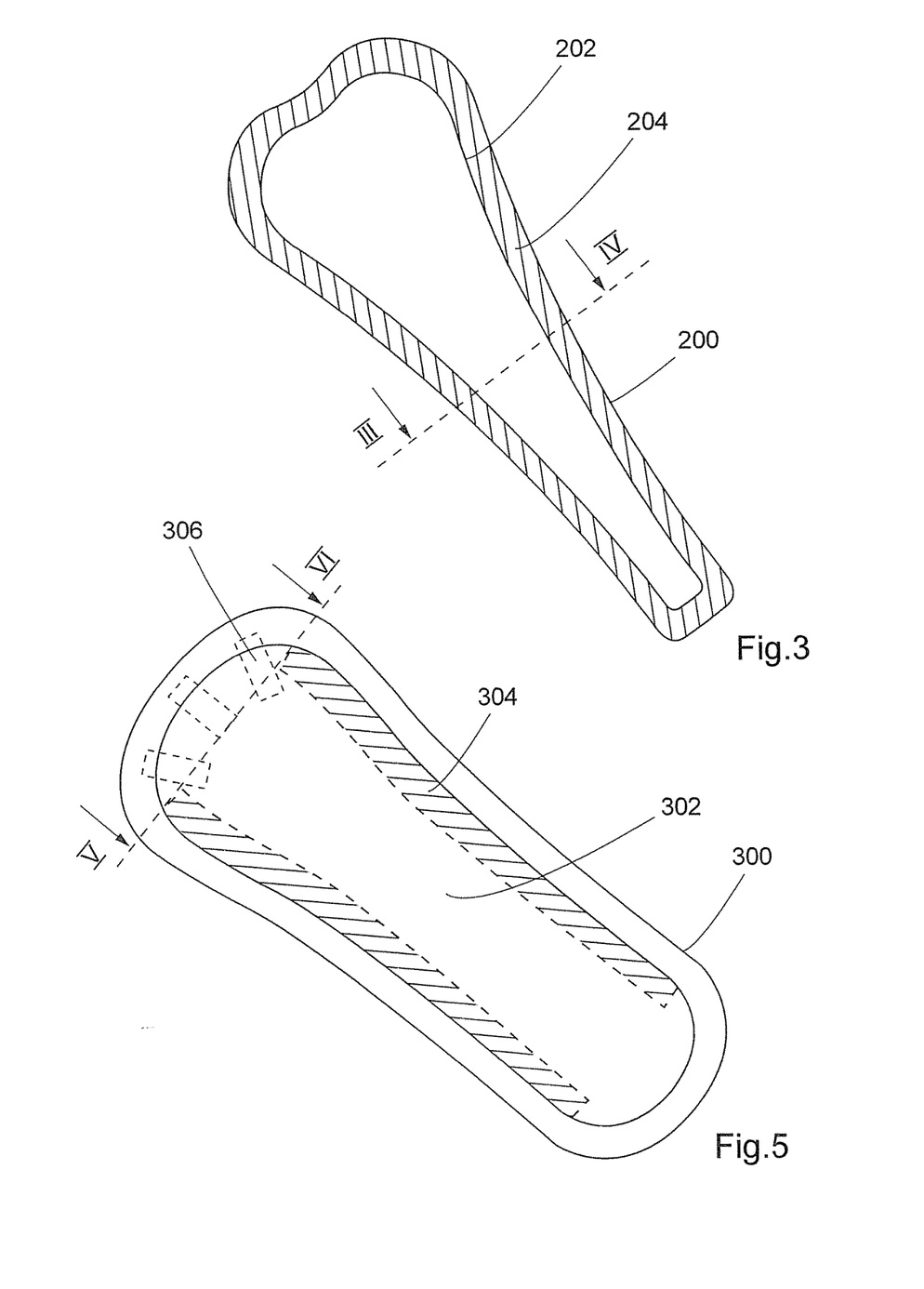
FIG. 3 relates to a panty liner wherein beads of a lipid phase containing a skin care agent have been arranged along the edges between the liquid pervious sheet and the liquid-impervious sheet.
FIG. 5 discloses a panty liner comprising both strips treated with a skin care agent is arranged between the absorbent core and a liquid previous sheet, and beads of a lipid phase containing a skin care agent have been arranged along the edges between the liquid pervious sheet and the liquid-impervious sheet.
Figure 4:
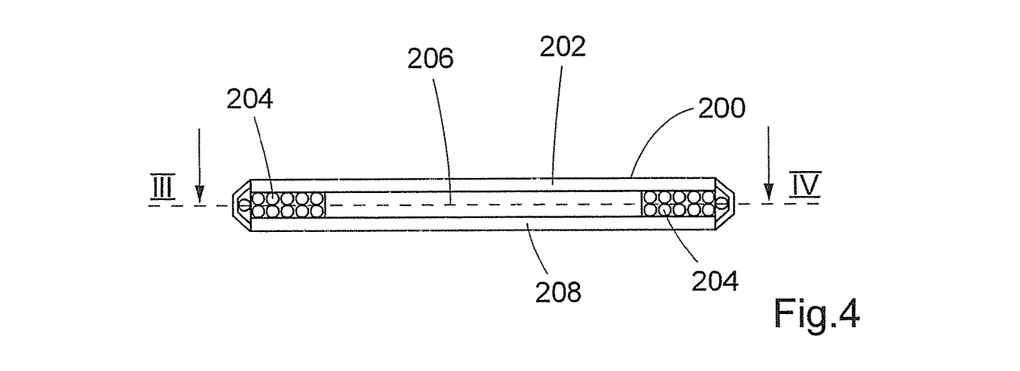
FIG. 4 shows a cross-section along III-IV of the panty liner of FIG. 3.

FIGS. 3 and 4 relate to a panty liner 200 comprising a liquid-pervious first sheet 202 intended to face the wearer, and a liquid-impervious second sheet 208 intended to face away from the wearer. An absorbent core 206 is located in the centre of the panty liner 200. Beads 204 of a lipid phase containing a skin care agent are arranged along the edges between the first sheet 202 and the second sheet 208 and adjacent to the absorbent core 206.

Example 3

Figure 6:
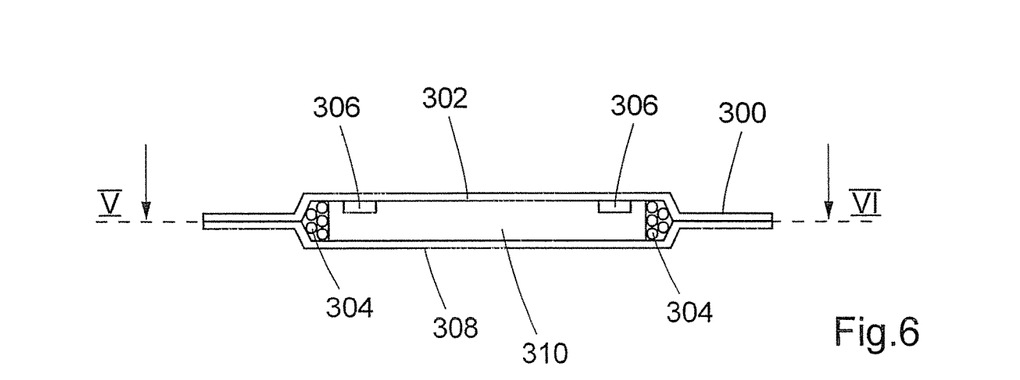
FIG. 6 shows a cross-section along V-VI of the panty liner of FIG. 5.

FIGS. 5 and 6 relate to a panty liner 300 comprising a liquid-pervious first sheet 302 intended to face the wearer, and a liquid-impervious second sheet 308 intended to face away from the wearer. An absorbent core 310 is located in the centre of the panty liner 300. Strips 306 treated with a skin care agent are arranged on top of the absorbent core 310 and below first sheet 302. Beads 304 of a lipid phase containing a skin care agent are arranged along the edges of the absorbent core 310 and between the first and second sheets 302, 308.

Example 4

Figure 7:
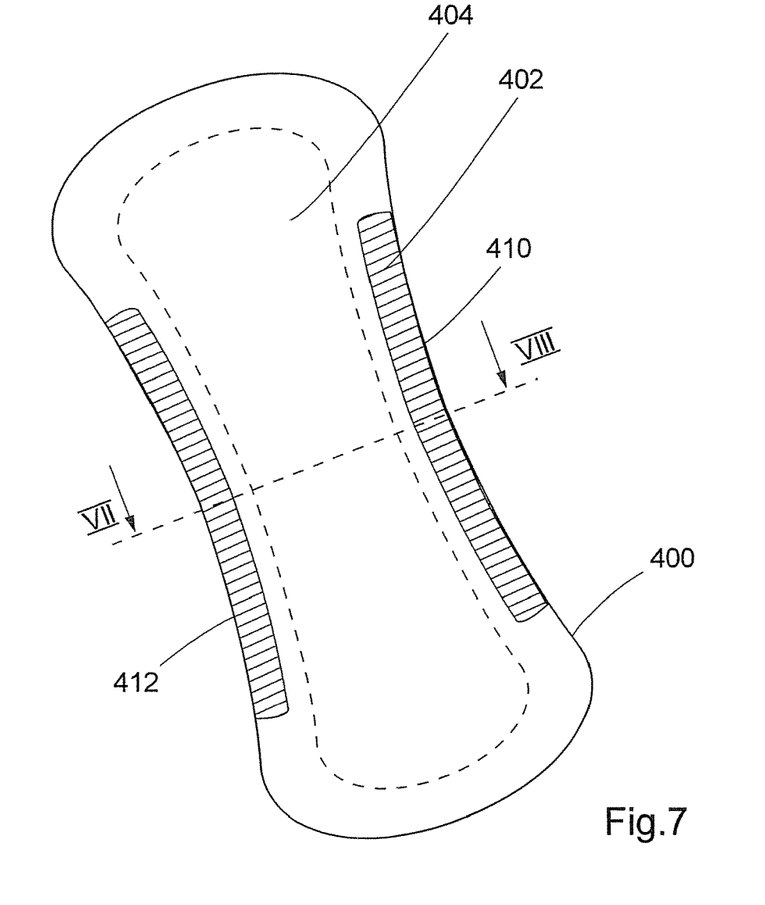
FIG. 7 describes a panty liner comprising strips treated with a skin care agent along two of the edges.
Figure 8:
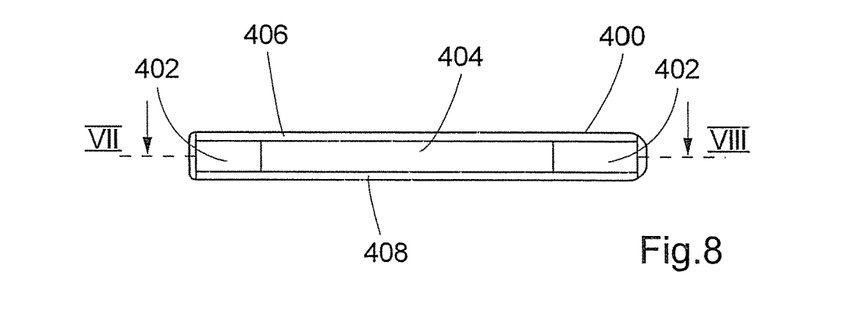
FIG. 8 shows a cross-section along VII-VIII of the panty liner of FIG. 7.

FIGS. 7 and 8 disclose a panty liner 400 comprising a liquid-pervious first sheet 406 intended to face the wearer, and a liquid-impervious second sheet 408 intended to face away from the wearer. An absorbent core 404 is located in the centre of the panty liner 400. Strips 402 treated with a skin care agent are arranged along the long edges 410, 412 of the panty liner 400 adjacent to the absorbent core 404 and between the first and second sheets 406, 408.

Example 5

Figure 9:
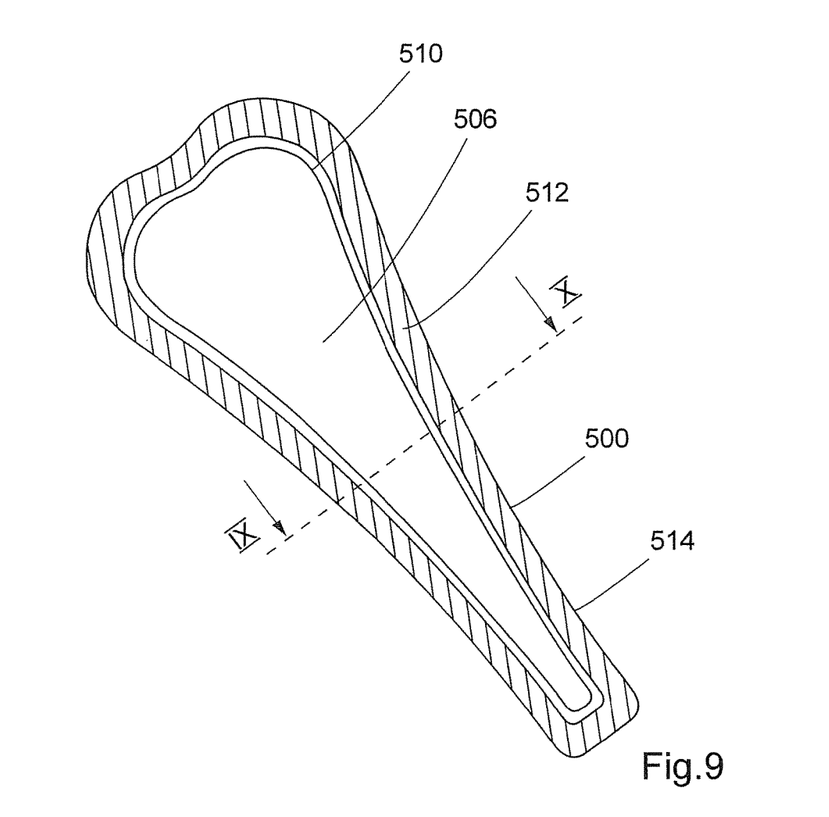
FIG. 9 discloses a panty liner wherein beads of a lipid phase containing a skin care agent have been arranged along the edges between the liquid pervious sheet and the liquid-impervious sheet, from the comparatively thicker central part to the thinner and more flexible edge parts.
Figure 10:
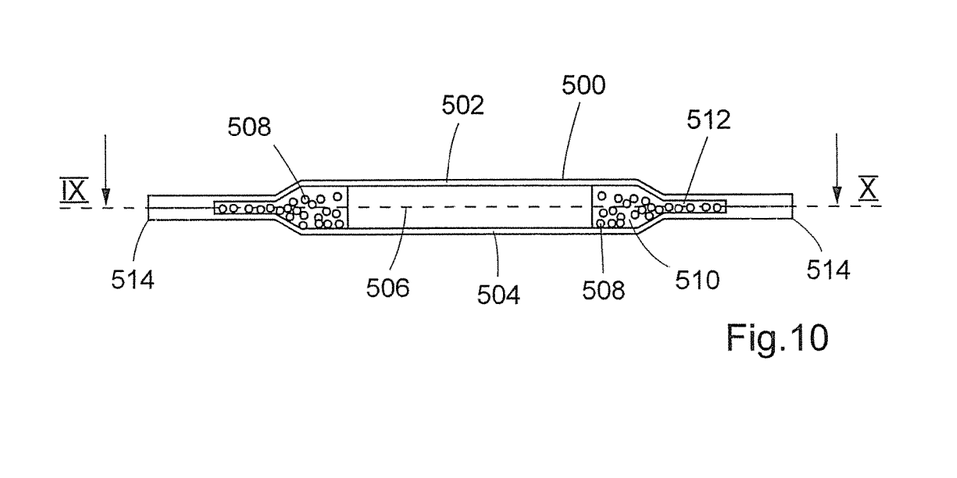
FIG. 10 shows a cross-section along IX-X of the panty liner of FIG. 9.

FIGS. 9 and 10 show a panty liner 500 comprising a liquid-pervious first sheet 502 intended to face the wearer, and a liquid-impervious second sheet 504 intended to face away from the wearer. An absorbent core 506 is located in the centre of the panty liner 500. Beads 508 of a lipid phase containing a skin care agent are arranged along the edges of the absorbent core. The beads 508 are arranged in both a thicker part 510 adjacent to the absorbent core, and a thinner part 512 at the flexible edges 514 of the panty liner.

Example 6

Figure 11:
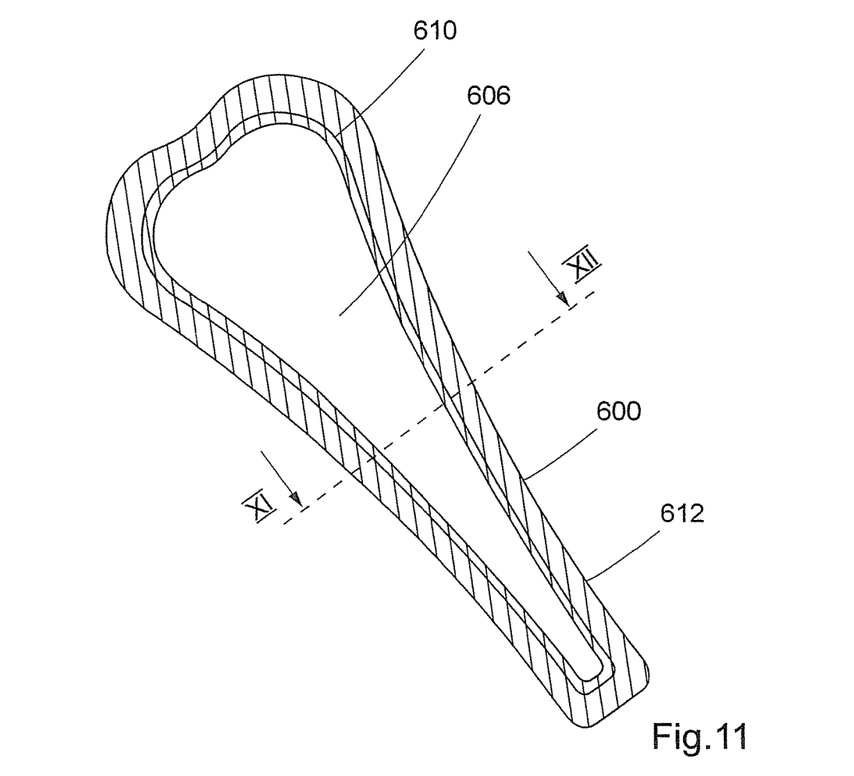
FIG. 11 discloses a panty liner wherein beads of a lipid phase containing a skin care agent have been arranged along the flexible edges between the liquid-pervious sheet and liquid-impervious sheet.
Figure 12:
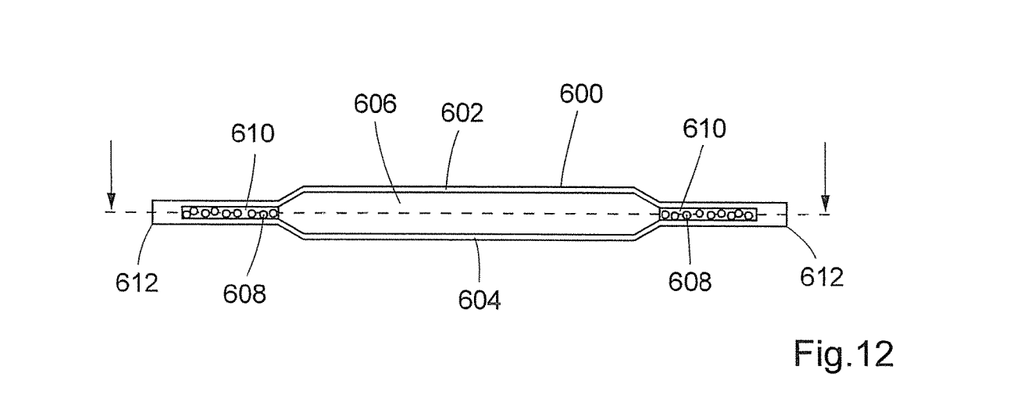
FIG. 12 shows a cross-section along XI-XII of the panty liner of FIG. 11.

FIGS. 11 and 12 disclose a panty liner 600 comprising a liquid-pervious first sheet 602 intended to face the wearer, and a liquid-impervious second sheet 604 intended to face away from the wearer. An absorbent core 606 is located in the centre of the panty liner 600. Beads 608 of a lipid phase containing a skin care agent are arranged along the edges of the absorbent core. The beads 608 are arranged in a thinner part 610 at the flexible edges 612 of the panty liner.

Although preferred embodiments have been depicted and described in detail herein, it will be apparent to those skilled in the relevant art that various modifications, additions, substitutions, and the like can be made without departing from the spirit of the invention, and these are thus considered to be within the scope of the invention as defined in the claims which follow, and equivalents thereof.

The invention claimed is:

1. An absorbent article comprising a liquid-pervious first sheet adapted to face a wearer, a liquid-impervious second sheet adapted to face away from the wearer, and a core part,
   the core part comprising an absorbent core, the absorbent core arranged between the first and second sheets, and an auxiliary component,
   the auxiliary component consisting of a layer of a lipid phase containing a skincare agent composition, wherein said skincare agent composition is immobilized in the lipid phase, wherein the lipid phase is solid at a temperature of 25° C. and is in a substantially liquid state at a temperature of 37° C., wherein the lipid phase is a water-insoluble organic phase with a fatty character, wherein said lipid phase is included as one or more beads,
   wherein said skincare agent composition comprises an emollient and an immobilizing agent for the emollient, wherein the emollient has either a plastic or fluid consistency at 20° C., and the immobilizing agent is miscible with the emollient and has a melting point of at least 35° C., and
   wherein the skin care agent composition comprises from about 10% to about 95% of the emollient.

2. The absorbent article according to claim 1, wherein said core part further comprises at least one nonwoven strip arranged between said first and second sheets, said strip being treated with the skincare agent composition in the form of one or more beads of lipid.

3. The absorbent article according to claim 2, wherein the nonwoven strip at least partially surrounds the absorbent core.

4. The absorbent article according to claim 1, wherein said lipid phase is included as one or more beads arranged between the absorbent core and the first sheet or second sheet.

5. The absorbent article according to claim 1, wherein said core part is treated with the skincare agent composition in a part adapted to face the inner part of a thigh of the wearer.

6. The absorbent article according to claim 1, wherein said core part is treated with the skincare agent composition in locations close to edges or wings of the article.

7. The absorbent article according to claim 1, wherein said lipid phase is included as one or more beads arranged between the absorbent core and the first and second sheet.

8. The absorbent article according to claim 1, wherein said absorbent article is chosen from the group of diapers, panty liners, sanitary napkins and incontinence guards.

9. The absorbent article according to claim 1, wherein the lipid is selected from the group consisting of petroleum-derived lipids, synthetic lipids, and animal- and plant-derived lipids.

10. The absorbent article according to claim 1, wherein the skin care agent composition comprises from about 20% to about 80% of the emollient.

11. The absorbent article according to claim 1, wherein the skin care agent composition comprises from about 40% to about 70% of the emollient.

12. An absorbent article comprising a liquid-pervious first sheet adapted to face a wearer, a liquid-impervious second sheet adapted to face away from the wearer, and a core part, the core part comprising an absorbent core, the absorbent core arranged between the first and second sheets, and an auxiliary component, said core part being at least partially treated with a first composition, wherein said first composition comprises from about 10% to about 95% of an emollient, the auxiliary component being a layer of a lipid phase, wherein a skincare agent composition is immobilized in the lipid phase, wherein said lipid phase is in the form of one or more beads of lipid.

13. The absorbent article according to claim 12, wherein said core part further comprises at least one nonwoven strip arranged between said first and second sheets, said strip being treated with the first composition in the form of one or more beads of lipid.

14. The absorbent article according to claim 13, wherein the nonwoven strip at least partially surrounds the absorbent core.

15. The absorbent article according to claim 12, wherein the beads of lipid are arranged between the absorbent core and the first or second sheet.

16. The absorbent article according to claim 12, wherein the beads of lipid are arranged between the absorbent core and the first and second sheet.

17. The absorbent article according to claim 12, wherein the lipid is selected from the group consisting of petroleum-derived lipids, synthetic lipids, and animal- and plant-derived lipids.

18. The absorbent article according to claim 12, wherein the first composition comprises from about 20% to about 80% of the emollient.

19. The absorbent article according to claim 12, wherein the first composition comprises from about 40% to about 70% of the emollient.

20. The absorbent article according to claim 12, wherein said core part is treated with the first composition in a part adapted to face the inner part of a thigh of the wearer.

21. The absorbent article according to claim 12, wherein said core part is treated with the first composition in locations close to edges or wings of the article.

22. The absorbent article according to claim 12, wherein said absorbent article is chosen from the group of diapers, panty liners, sanitary napkins and incontinence guards.

23. An absorbent article comprising:

a liquid-pervious first sheet adapted to face a wearer;

a liquid-impervious second sheet adapted to face away from the wearer;

a core part including an absorbent core arranged between the first and second sheets;

an auxiliary component, the auxiliary component being an independent layer of a lipid phase comprising a skin care composition, the lipid phase being solid at a temperature of 25° C. and in a substantially liquid state at a temperature of 37° C., wherein said lipid phase is in the form of one or more beads of lipid; and a skincare agent composition, the skincare agent composition comprising an emollient, wherein said skincare agent composition is immobilized in the lipid phase.

* * * * *